United States Patent
Homan et al.

(10) Patent No.: US 7,452,328 B2
(45) Date of Patent: Nov. 18, 2008

(54) CAPSULE ENDOSCOPE APPARATUS

(75) Inventors: Masatoshi Homan, Hino (JP); Wataru Ohno, Hachioji (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 10/823,832

(22) Filed: Apr. 14, 2004

(65) Prior Publication Data
US 2004/0215059 A1    Oct. 28, 2004

(30) Foreign Application Priority Data
Apr. 25, 2003  (JP) .............................. 2003-122821

(51) Int. Cl.
*A61B 1/06* (2006.01)
(52) U.S. Cl. .................. 600/180; 600/101; 600/109; 600/160; 600/178; 600/179
(58) Field of Classification Search .................. 600/180
See application file for complete search history.

(56) References Cited

U.S. PATENT DOCUMENTS

| 5,604,531 | A  |   | 2/1997  | Iddan et al. |
|-----------|----|---|---------|--------------|
| 6,667,765 | B1 | * | 12/2003 | Tanaka ..................... 348/229.1 |
| 6,724,418 | B1 | * | 4/2004  | Takahashi .................... 348/65 |
| 6,951,536 | B2 | * | 10/2005 | Yokoi et al. .................. 600/128 |
| 2003/0023150 | A1 |   | 1/2003 | Yokoi et al. |
| 2003/0028078 | A1 | * | 2/2003 | Glukhovsky ................. 600/109 |
| 2003/0117491 | A1 |   | 6/2003 | Avni et al. |
| 2003/0174208 | A1 |   | 9/2003 | Glukhovsky et al. |

FOREIGN PATENT DOCUMENTS

| EP | 0 912 047 A2 | 4/1999 |
|----|--------------|--------|
| EP | 1 326 432 A2 | 7/2003 |
| JP | 11-155808    | 6/1999 |
| JP | 2000-125185  | 4/2000 |
| JP | 2000-262369  | 9/2000 |
| JP | 2003-038425  | 2/2003 |
| JP | 2003-265405  | 9/2003 |
| WO | WO 03/009739 A2 | 2/2003 |

* cited by examiner

*Primary Examiner*—Linda C Dvorak
*Assistant Examiner*—Matthew J Kasztejna
(74) *Attorney, Agent, or Firm*—Scully, Scott, Murphy & Presser, P.C.

(57) ABSTRACT

A capsule endoscope apparatus includes an illuminating device, an image pick-up device which picks up an image of an illuminated portion, and a radio transmitting device. The illuminating device in the capsule endoscope apparatus has a switching device which switches two or more light-emitting amount or light-emitting time. The radio transmitting device in the capsule endoscope apparatus transmits by radio waves image data obtained by the image pick-up device upon sequentially switching the two or more light-emitting amount or light-emitting time.

25 Claims, 11 Drawing Sheets

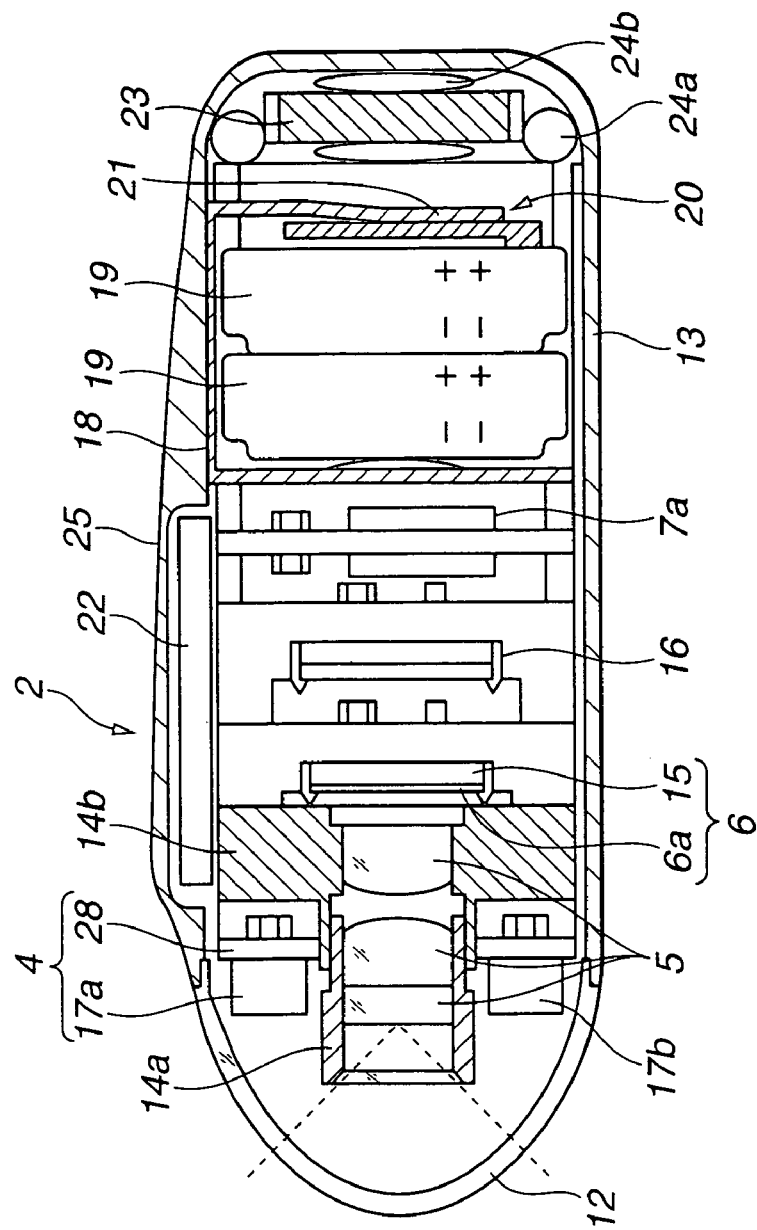
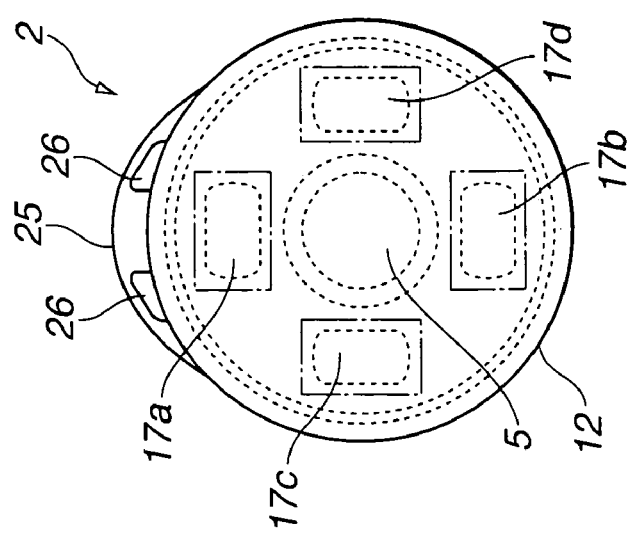
FIG.4A
FIG.4B

CAPSULE ENDOSCOPE APPARATUS

This application claims benefit of Japanese Application No. 2003-122821 filed on Apr. 25, 2003, the contents of which are incorporated by this reference.

BACKGROUND OF THE INVENTION

1. Field of the Invention

The present invention relates to a capsule endoscope apparatus which picks up an image of the body cavity.

2. Description of the Related Art

For example, U.S. Patent Publication No. 5,604,531 discloses, as one conventional art, an observing system of the interior of the body. According to the one conventional art, an image picked up by an image pick-up unit is extracorporeally transmitted by radio waves, is received by an extracorporeal device, and is stored. Then, the stored image is displayed and the position of the image pick-up unit is displayed.

Referring to FIG. 1, a capsule endoscope system 81 according to another conventional art comprises: a capsule endoscope apparatus 82 which is swallowed by a patient and which then picks up an image of the body cavity; and an extracorporeal device 83 which is extracorporeally arranged to the patient.

The capsule endoscope apparatus 82 comprises in a capsule container: illuminating means 84; an objective lens 85 which forms an image; image pick-up means 86 which is arranged at the image forming position and which picks up the image; and radio means 87 which transmits by radio waves an image signal picked up by the image pick-up means 86.

Further, the extracorporeal device 82 comprises: radio means 88 which receives the image signal transmitted by radio waves from the radio means 87 in the capsule endoscope 82; and recording means 89 which records the image signal that is demodulated by the radio means 88.

According to the other conventional art, referring to FIG. 2A, in the illuminating means 84, a white LED 93 is switched on/off at a predetermined interval via an electric switch 92 from a constant-current source 91, thus to emit light as shown in FIG. 2B.

In this case, a light-emitting amount L and a light-emitting time t are constant and the term is an image pick-up term T.

According to the conventional arts shown in FIGS. 1, 2A, and 2B, upon picking up an image of the body cavity, the distance from the capsule endoscope 82 to, e.g., the inner wall of the gastrointestinal tract as an observed target varies depending on the portion.

In this case, a light-emitting value of the illuminating means 84 which emits pulse light is constant, then, if the capsule endoscope is too much close to the observed target, the white compression is caused, and if it is too much apart from it, the black compression is caused.

SUMMARY OF THE INVENTION

According to the present invention, a capsule endoscope apparatus having an illuminating device, an image pick-up device for picking up an image of an illuminated portion, and a radio transmitting device, comprises:

the illuminating device comprising a switching device which switches two or more light-emitting amount or light-emitting time; and a radio device which transmits by radio waves image data obtained by the image pick-up device upon sequentially switching the two or more light-emitting amount or light-emitting time.

BRIEF DESCRIPTION OF THE DRAWINGS

FIGS. 3 to 11 relate to a first embodiment of the present invention,

FIG. 3 is a diagram showing the entire structure of a capsule endoscope system according to the first embodiment;

FIGS. 4A and 4B are a cross-sectional view and a front view showing the specific structure of a capsule endoscope (apparatus), respectively;

FIG. 6 is a characteristic diagram showing an example of a light-emitting characteristic of a white LED;

FIG. 7 is a block diagram showing the structure of illuminating means according to a first modification of the first embodiment;

FIG. 8 is a block diagram showing the structure of illuminating means according to a second modification of the first embodiment;

FIG. 9 is an explanatory diagram showing the light-emitting operation of the illuminating means;

FIG. 10 is a block diagram showing the structure of image pick-up means according to a third modification of the first embodiment;

FIG. 11 is a block diagram showing the structure of illuminating means according to a fourth modification of the first embodiment;

FIGS. 12A to 13 relate to a second embodiment of the present invention,

FIG. 12A is a diagram schematically showing a capsule endoscope according to the second embodiment;

FIG. 13 is a diagram schematically showing an extracorporeal device according to a second modification of the second embodiment;

FIG. 14 is a block diagram showing the structure of illuminating means according to the third embodiment;

FIG. 15 is an explanatory diagram of the light-emitting operation of the illuminating means;

FIG. 16 is a diagram schematically showing a capsule endoscope according to the fourth embodiment;

FIG. 17 is a block diagram showing the structure of image processing means;

FIG. 18 is a diagram schematically showing an extracorporeal device according to a modification of the fourth embodiment;

FIG. 19 is a block diagram showing the structure of illuminating means according to the fifth embodiment; and FIG. 20 is an explanatory diagram of the light-emitting operation.

DESCRIPTION OF THE PREFERRED EMBODIMENTS

Hereinbelow, the first embodiment of the present invention will be described with reference to the drawings.

First Embodiment

A description is given of the first embodiment of the present invention with reference to FIGS. 3 to 11.

Figure 3:
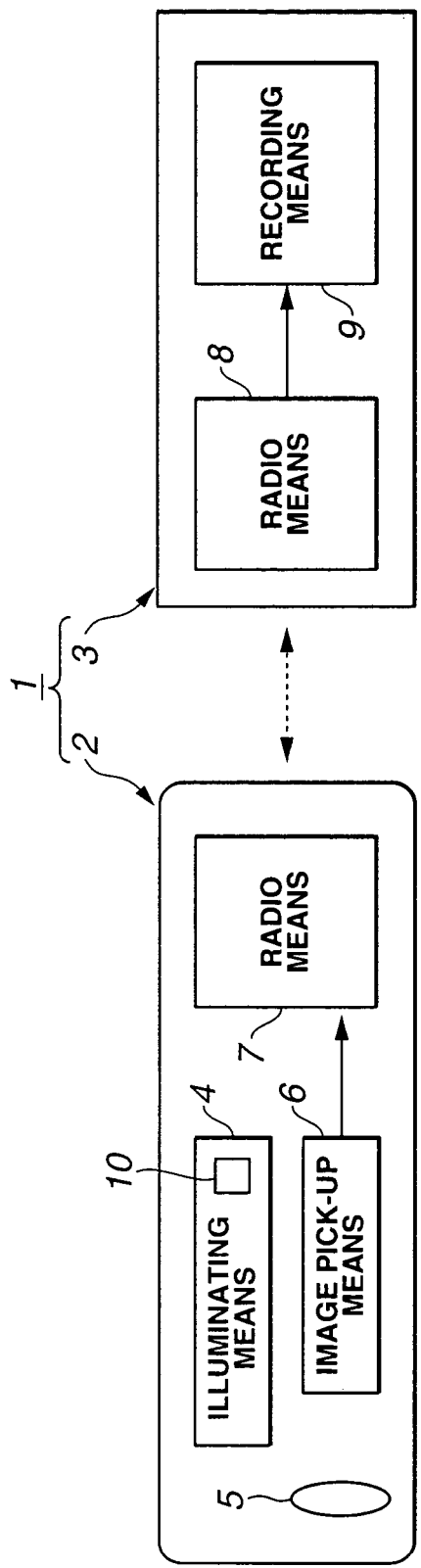

Referring to FIG. 3, a capsule endoscope system 1 according to the first embodiment of the present invention comprises: a capsule endoscope apparatus (hereinafter, abbreviated to a capsule endoscope) 2 which is swallowed by a patient and which then picks up an image of the body cavity; and an extracorporeal device 3 which receives and records image data from the capsule endoscope 2.

The capsule endoscope 2 comprises in a capsule container: illuminating means 4; an objective lens 5 which forms an image; image pick-up means 6 which is arranged at the image forming position thereof and which picks up the image; and radio means 7 which transmits by radio waves an image signal picked up by the image pick-up means 6. As will be described later, the illuminating means 4 has light-emitting amount varying means 10 which variably sets the light-emitting amount of a light-emitting device.

The extracorporeal device 3 comprises: radio means 8 which receives the image signal transmitted by radio waves from the radio means 7 in the capsule endoscope 2; and recording means 9 which records the image signal demodulated by the radio means 8.

FIGS. 4A and 4B show the specific structures of the capsule endoscope 2. FIG. 4A shows a longitudinal cross-sectional view of the capsule endoscope 2, and FIG. 4B shows a front view thereof.

The capsule endoscope 2 is airtightly covered with a transparent dome (edge cover) 12 which is transparent on the edge side. In the transparent dome 12, an (airtightly covered) cylindrical capsule container is formed by airtightly being jointed to the rear edge of an exterior case 13 which has a rear edge closed and which is approximately cylindrical. The capsule container includes components such as white LEDs 17*a* to 17*d* as light emitting devices forming the above-mentioned illuminating means 4 and an image pick-up element 6*a* forming the image pick-up means 6.

Specifically speaking, the capsule endoscope 2 has an objective lens 5 which is attached to two lens frames 14*a* and 14*b* in the center of the capsule container on the edge side, and further has the image pick-up element 6*a* at the image forming position of the objective lens 5.

An image pick-up and driving circuit 15 which drives the image pick-up element 6*a* is arranged around the image pick-up element 6*a*. The image pick-up element 6*a* and the image pick-up and driving circuit 15 form the image pick-up means 6.

The image pick-up and driving circuit 15 applies a driving signal to the image pick-up element 6*a* (by its driving circuit), the image pick-up element 6*a* outputs an image pick-up signal which is photoelectrically converted, and (an image pick-up circuit of) the image pick-up and driving circuit 15 amplifies the signal and converts the signal into a digital signal.

A digital signal processing circuit 16 for compression processing of the digital signal from the image pick-up and driving circuit 15 is arranged on the back side of the image pick-up and driving circuit 15 and the image pick-up element 6. The digital signal processing circuit 16 performs the compression processing of a digital image signal (image data), and forms the compressed image data. A radio receiving and transmitting circuit 7*a* forming the radio means 7 is arranged on the back side of the digital signal processing circuit 16 so as to transmit the compressed image data by radio waves.

Referring to FIG. 4B, around the objective lens 5, the four white LEDs 17*a* to 17*d* are arranged at different positions facing them on the top and bottom, and right and left as the light emitting devices forming the illuminating means 4. The white LEDs 17*a* to 17*d* illuminate the front side of the capsule endoscope 2 via the transparent dome 12. Incidentally, the four white LEDs 17*a* to 17*d* forming the illuminating means 4 are abbreviated by reference numeral 17 when they are simultaneously driven.

On the back surface of the radio receiving and transmitting circuit 7*a*, a battery accommodating unit 18 is arranged. Two batteries 19 such as button batteries are accommodated in the battery accommodating unit 18. An operating switch 20 is arranged at the rear end of the battery accommodating unit 18.

The two batteries 19 are serially connected, its negative electrode is pressed and connected to the GND of the radio receiving and transmitting circuit 7*a*, and its positive electrode is connected to a fixing plate side. A plate spring 21 as a movable plate facing the fixing plate is connected to a power supply end of the radio receiving and transmitting circuit 7*a* or the like via a flexible substrate which is arranged along the outer peripheral surface of the battery accommodating unit 18. When the fixing plate is contact with the plate spring 21, the operating switch 20 is turned on, and then power for operation is supplied to the radio receiving and transmitting circuit 7*a*.

A radio antenna 22 is arranged adjacently to the image pick-up element 6*a*.

The capsule endoscope 3 has the capsule container which is set to easily be swallowed by the patient.

When the capsule endoscope 3 stops in the luminal portion of the body cavity, a permanent magneto 23 is accommodated at the rear end facing the operating switch 20 so as to collect the stopped capsule endoscope 3 by a string collecting tool (not shown) having a magneto at the edge thereof.

The permanent magneto 23 is also used for a switch driving mechanism for switching from off to on the operating switch 20.

The permanent magneto 23 can be moved on a guide rail 24*a* made of smooth plastic material. The movement of the magneto 23 is pressed by an energizing member 24*b* made of an elastic rubber and is restricted on the guide rail 24*b*.

The permanent magneto 23 is moved from one end portion of the guide rail 24*a* to another end portion by using a permanent magneto (not shown) which is externally arranged. When the permanent magneto 23 is moved to the other end portion, the size of a magnetic field which operates to the operating switch 20 using the permanent magneto 23 is reduced.

The operating switch 20 has the plate spring 21 having the magnetized end portion, facing the fixing plate conductive to the battery 19. Referring to FIG. 4A, the shape of the end portion of the plate spring 21 is processed so as to be contact with the fixing plate. When the permanent magneto 23 is arranged at the position facing the plate spring 21, the plate spring 21 can be apart from the fixing plate by absorbing force generated by the magnetic field. That is, when the permanent magneto 23 is arranged facing the plate spring 21, the operating switch 20 is turned off.

The permanent magneto which is externally arranged moves the permanent magneto 23 from the one position facing the end portion of the plate spring 21 to the other position, thereby reducing the magnetic field operated to the plate spring 21 and turning on the operating switch 20. That is, referring to FIG. 4A, the permanent magneto 23 is moved from the one position facing the end portion of the plate spring 21 to the other position.

According to the first embodiment, the capsule container has an extending portion 25 having a large cross-section in the one-axis direction which is approximately circular, and further has a vertical cross-section which becomes a non-circular cross-section. In the capsule container, two bypassing holes 26 are formed to the extending portion 25 as fluid passages for bypassing fluid such as gas or body fluid before/after the luminal portion.

Thus, the capsule container enables the connection of the fluid such as gas or body fluid before/after the luminal portion of the body cavity via the bypassing holes 26.

Further, according to the first embodiment, the white LED 17 forming the illuminating means 4 is attached to an LED driving substrate 28. The LED driving substrate 28 forms a light-emitting driving circuit 29 (refer to FIG. 5A) which emits the white LED on pulse.

The light-emitting driving circuit 29 has light-emitting amount varying means 10. Further, referring to FIG. 5B, the light-emitting driving circuit 29 forms switching means which sequentially switches the light-emitting amount so as to emit light while changing the light-emitting amount of the four white LEDs 17 into two light-emitting amount L1 and L2 and sequentially change the light-emitting amount.

Figure 5B:
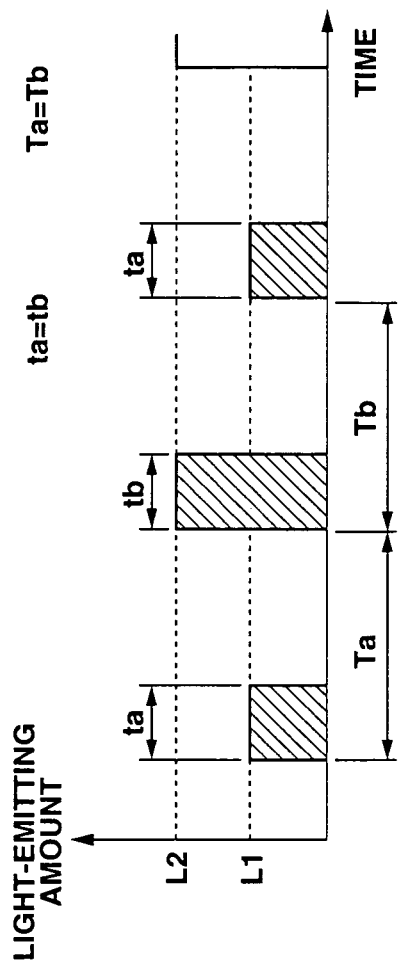
FIG. 5B is a diagram showing the light-emitting operation.
Figure 5A:
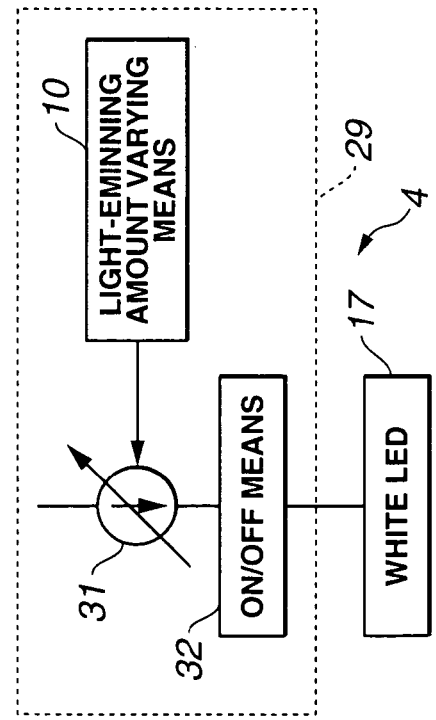
FIG. 5A is a diagram showing the structure of illuminating means.

FIG. 5A shows the structure of the illuminating means 4 having the light-emitting driving circuit 29. Referring to FIG. 5A, the illuminating means 4 comprises: a constant-current source 31 which can vary and set a constant current-value; ON/OFF means 32 which switches on/off the current from the constant-current source 31; the white LED 17 which emits pulse light by the supply of the constant current via the ON/OFF means 32; and the light-emitting varying means 10 which varies the light-emitting amount from the white LED 17 by varying and setting the value of the constant current of the constant-current source 31.

The constant-current source 31, the ON/OFF means 32, and the light-emitting amount varying means 10 form the light-emitting driving circuit 29.

According to the first embodiment, specifically, the four white LEDs 17 are used. Therefore, when the four white LEDs 17 shown in FIG. 5A are simultaneously driven, driving current of the four white LEDs 17 is changed.

Figure 6:
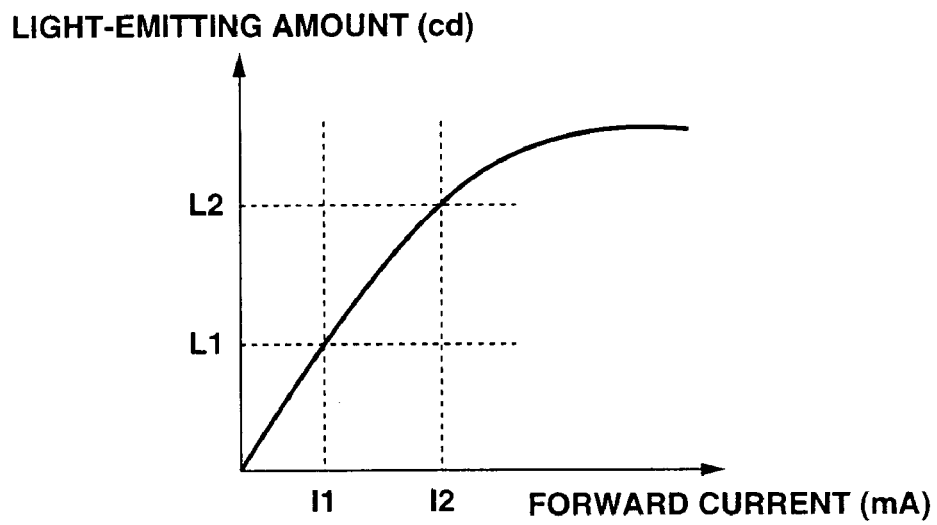

FIG. 6 shows a relationship between the light-emitting amount and forward (direction) current flowing to the white LEDs 17 in this case. An area where the light-emitting amount increases upon increasing the forward current is used for the emission of pulse light.

According to the first embodiment, referring to FIG. 6, the white LEDs 17 emit pulse light alternately (sequentially) as shown in FIG. 5B by current I1 having a light-emitting amount L1 and current I2 having a light-emitting amount L2 which are shown in FIG. 6.

The side of the observing target portion in the body cavity is sequentially illuminated by different light-emitting amount (amount of illuminating light). Under the illumination, the image pick-up means 6 picks up the images, thereby obtaining two images picked by the image pick-up means 6 with the different amount of illuminating light.

That is, according to the first embodiment, referring to FIG. 5B, light-emitting time ta and tb are constant and, however, the light-emitting amount L1 and L2 are sequentially changed and emitted. Further, the light-emitting amount L1 is emitted only for the light-emitting time Ia and ten light emission stops. Next, an image pick-up time Ta until the light emission wit the light-emitting amount L2 is the same as the image pick-up time Tb for a time period for which the light-emitting amount L2 is emitted only for a light-emitting time tb, then, the light emission stops, and the light-emitting amount L1 is emitted.

As mentioned above, according to the first embodiment, the images are picked up with different amount of illuminating light, the picked-up images are converted into the compressed image data, and they are transmitted to the radio means 8 in the extracorporeal device 3 by the radio means 7. Then, the image data received by the radio means 8 is recorded to the recording means 9 on the extracorporeal device 3 side.

The extracorporeal device 3 is connected to image display means, the image data recorded to the recording means 9 is subjected to decompression processing, the image picked up by the image pick-up means 6 is restored, and the restored is displayed by display means.

The image data picked up wit the different amount of illuminating light is recorded (stored) in the recording means 9 and medical staff (e.g., an operator) uses the image data wit preferable image quality for the diagnosis or the like.

The operation with the above-mentioned structure will be described according to the first embodiment.

The operating switch 20 in the capsule endoscope shown in FIG. 3 or 4A is turned on and then the capsule endoscope 2 is swallowed by a patient.

Then, the battery 19 supplies power for operation to the illuminating means 4, or the like. Referring to FIG. 5A, the white LED 17 forming the illuminating means 4 is driven so as to emit pulse light by the light-emitting driving circuit 29. Further, the light-emitting amount varying means 10 alternately emits pulse light with different light-emitting amount.

That is, referring to FIG. 5B, the light-emitting amount L1 is emitted, and the image pick-up means 6 picks up the image for the time ta with the light-emitting amount L1. The picked-up image is transmitted to the extracorporeal device 3 side within the image pick-up term Ta shown in FIG. 5B.

The image picked up by the image pick-up means 6 is converted into a digital signal by the digital signal processing circuit 16. Further, the digital signal is converted into the compressed image data. Thereafter, the image data is transmitted to the radio means 7, is modulated by an RF signal, and is externally transmitted by radio waves from the antenna 22.

On the extracorporeal device 3 side, the transmitted image data is demodulated by the radio means 8, and is recorded to the recording means 9.

After the image pick-up term Ta, the white LED 17 emits pulse light with the larger light-emitting amount L2. Similarly to the case of the pulse light with the light-emitting amount L1 within the image pick-up term Tb (=Ta), the picked-up image is transmitted to the extracorporeal device 3 side. On the extracorporeal device 3 side, the received image data is recorded to the recording means 9.

Next, the white LED 17 emits pulse light with the smaller light-emitting amount L1 again.

As mentioned above, according to the first embodiment, the subject is sequentially illuminated with the different light-emitting amount, the picked-up image data is transmitted, and is recorded by the extracorporeal device 3.

Therefore, the extracorporeal device 3 obtains the sequentially picked-up images with the different light-emitting amount. Thus, when the image of the observing target portion is picked up at the near-point, the image picked up with the smaller light-emitting amount L1 is used for the diagnosis. Thus, the image with smaller white compression is obtained.

When the image of the observing target portion is picked up from the far place, the image picked up with the larger light-emitting amount L2 is used for the diagnosis. Thus, the image with smaller black compression is obtained.

As mentioned above, according to the first embodiment, the subject is illuminated while switching the light-emitting amount and the image is picked up while illuminating the subject. Consequently, a plurality of images are obtained with different amount of illuminating light. By selecting one of the plurality of images, the image with smaller white compression and black compression is used for the diagnosis.

According to the first embodiment, the image which facilitates the endoscope examination and the diagnosis is provided. For the purpose of a brief description, according to the first embodiment, a description is given of the example of emitting light with the two different light emitting amount L1 and L2. By emitting light with three or more different light-emitting amount, the images may be picked up with the three or more amount of illuminating light.

Further, a condition for picking up the images with different amount of illuminating light may be selected and set.

Figure 7:
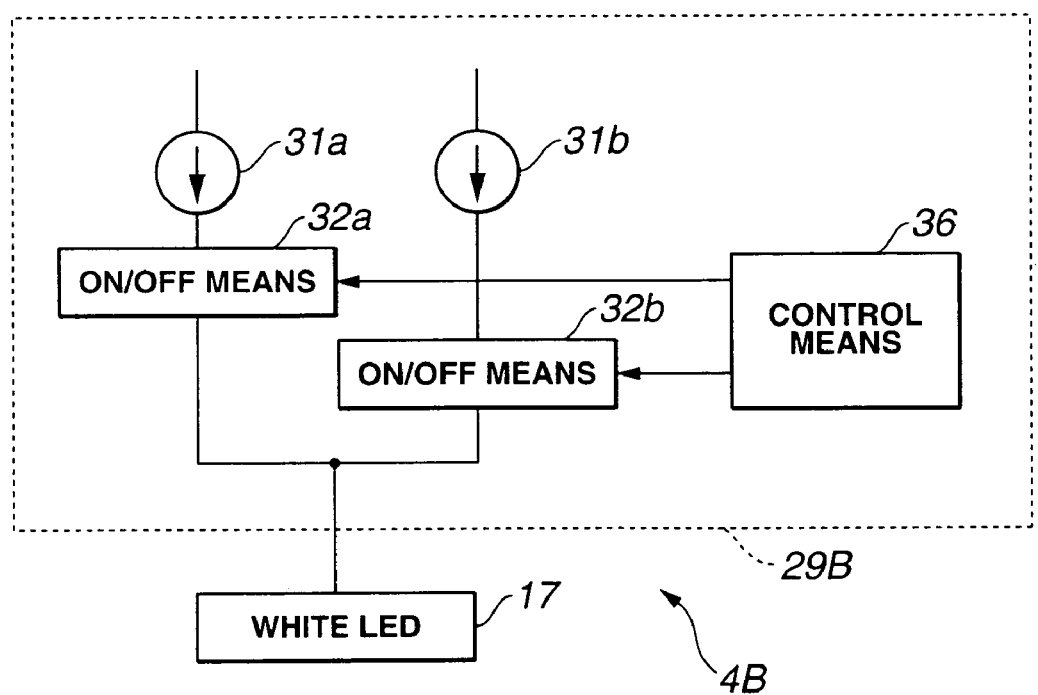

FIG. 7 shows the structure of illuminating means 4B according to a first modification of the first embodiment. Although one constant-current source is used as shown in FIG. 5A, two constant-current sources 31a and 31b are used as shown in FIG. 7.

That is, in the illuminating means 4B, the constant-current sources 31a and 31b are connected so as to supply constant current to the white LED 17 via serial ON/OFF means 32a and 32b. Further, a light-emitting driving circuit 29B is used to control the ON/OFF operation of the ON/OFF means 32a and 32b by control means 36.

For example, the ON/OFF means 32a connected to the one constant-current source 31a is turned on for the light-emitting time ta and tb with the light-emitting amount L1 and L2 shown in FIG. 5B. The other ON/OFF means 32b is turned on for the light-emitting time tb with the light-emitting amount L2 shown in FIG. 5B.

As mentioned above, the operation and advantage similar to those according to the first embodiment are obtained according to the first modification.

Figure 8:
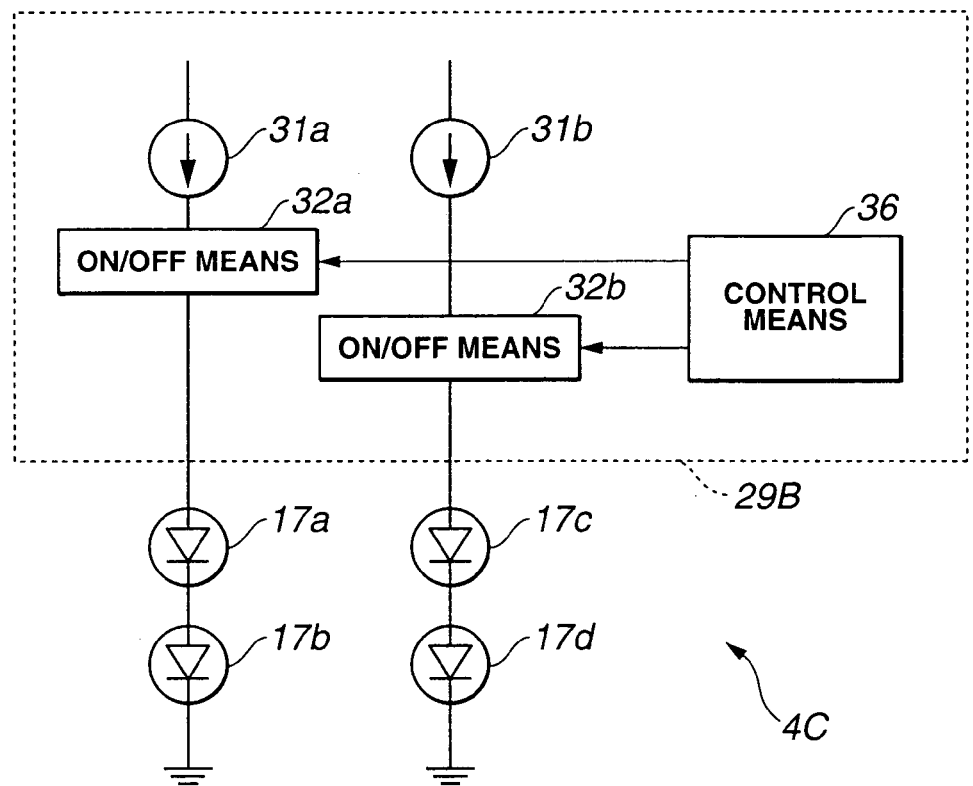

Further, illuminating means 4C may be used according to the second modification of the first embodiment as shown in FIG. 8. Although the four white LEDs 17 are simultaneously driven as shown in FIGS. 5A and 7, the white LED which emits light is selected, thereby emitting light with, e.g., two light-emitting amount as shown in FIG. 8.

Specifically, in the illuminating means 4C shown in FIG. 8, two white LEDs 17a and 17b are serially connected to the ON/OFF means 32a shown in FIG. 7, and two other white LEDs 17c and 17d are serially connected to the ON/OFF means 32b.

Figure 9:
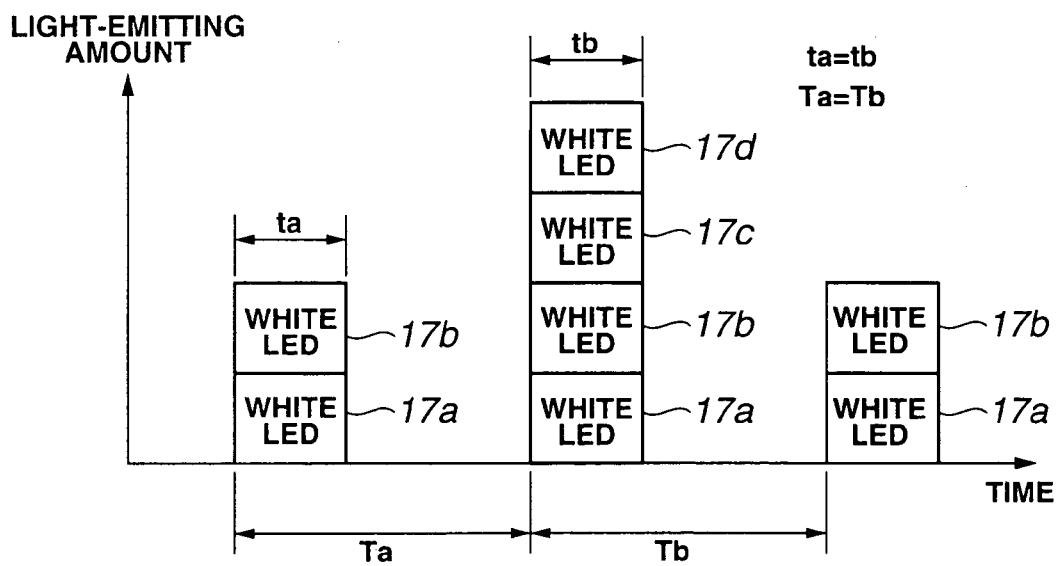

The ON/OFF means 32a and 32b is driven by the control means 36 similarly to the case described with reference to FIG. 7 and thus light-emitting operation is performed as schematically shown in FIG. 9.

That is, at the light-emitting time ta, the ON/OFF means 32a is turned on so that the white LEDs 17a and 17b emit light.

After the image pick-up time Ta including the light-emitting time ta, the ON/OFF means 32a and 32b are turned on so that the white LEDs 17a, 17b, 17c, and 17d emit light.

In this case, when the white LEDs 17a and 17b emit light by the constant current from the constant-current source 31a, the light-emitting amount corresponds to the light-emitting amount L1 shown in FIG. 5B. When the white LEDs 17a to 17d simultaneously emit light by the constant current of the constant-current sources 31a and 31b, the light-emitting amount corresponds to the light-emitting amount L2 shown in FIG. 5B.

The operation and advantage in this case are similar to those according to the first modification.

Figure 10:
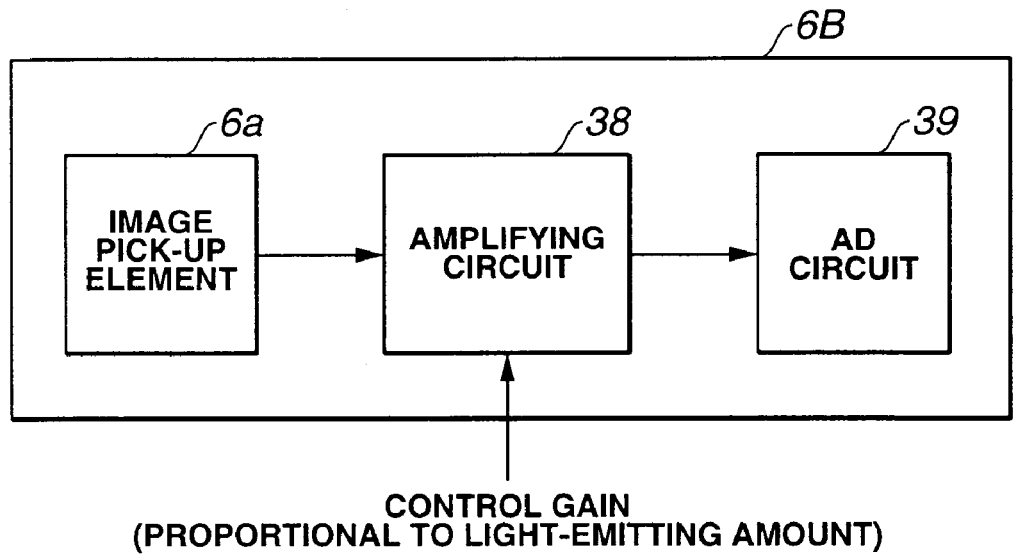

FIG. 10 schematically shows the structure of image pick-up means 6B according to the third modification. According to the third modification, the image pick-up means 6B comprises: an image pick-up element 6a for image pick-up operation; an amplifying circuit 38 which amplifies an output signal from the image pick-up element 6a; and an A/D circuit 39 which converts the signal amplified by the amplifying circuit 38 into a digital signal.

According to the third modification, the light-emitting varying means 10 shown in FIG. 5A controls the gain of the amplifying circuit 38 synchronously with the change in light-emitting amount by a gain control signal.

Specifically, the gain is reduced in the case of the light-emitting amount L1, and the gain is increased in the case of the light-emitting amount L2. As a typical example, the light-emitting amount and the gain are proportionally controlled. As mentioned above, the varying operation of the gain is controlled synchronously with the light emission, thereby improving the function in the case of changing the light-emitting amount.

In this case, a control signal may be transmitted to the capsule 2 from the extracorporeal device 3 side, and the gain may be varied and controlled by the control signal. For example, referring to FIG. 18, in an extracorporeal device 3C, display means 59 may display the image transmitted from the capsule 2 side. A control signal for controlling the gain may be transmitted to the capsule endoscope from the extracorporeal device 3C side so that the operator sets the image more preferable than the image in such a state based on the observation of the image.

Figure 11:
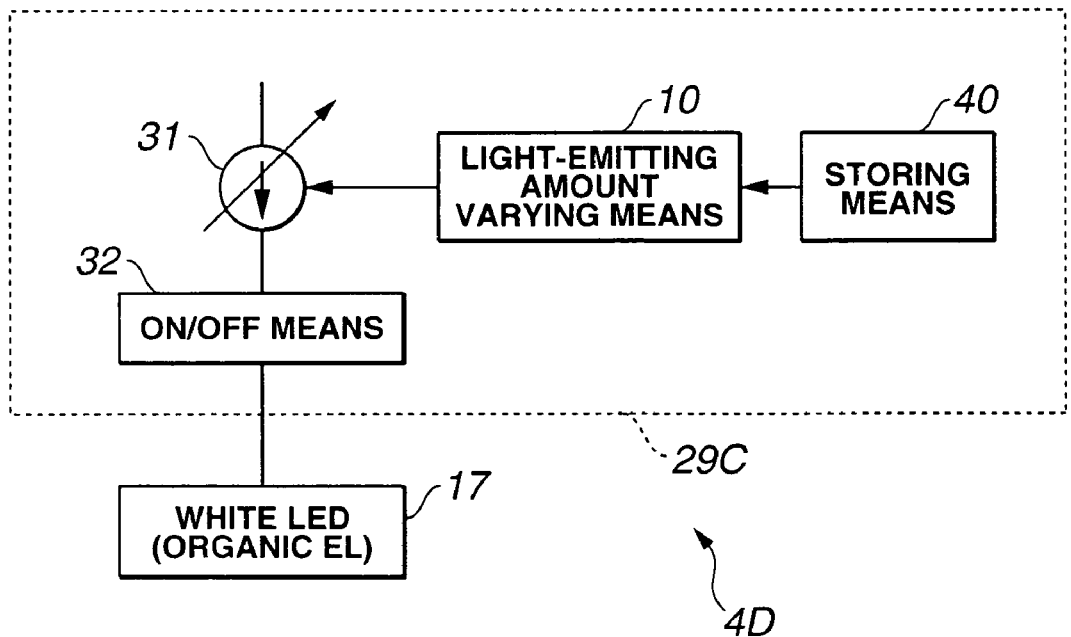

FIG. 11 shows the structure of illuminating means 4D according to the fourth modification of the first embodiment. In the illuminating means 4 shown in FIG. 5A, light-emitting setting means for setting the light-emitting amount switched and set by the light-emitting amount varying means 10 is a light-emitting driving circuit 29C having storing means 40 such as a memory for storing information that determines the light-emitting amount.

The storing means 40 previously stores the information that determines the light-emitting amount of the light-emitting varying means 10 in accordance with the examining target portion using the capsule endoscope including the illuminating means 4D, thus setting the illuminating state in which the light is emitted with the proper light-emitting amount.

Therefore, the storing means 40 may comprise a non-volatile memory such as a flash memory which can electrically be written.

Information for controlling the light-emitting amount from the light-emitting amount varying means 10 is transmitted by radio waves to the radio means 7 in the capsule endoscope including the illuminating means 4D via the radio means 8 from the extracorporeal device 3 side. The capsule endoscope stores the information for controlling the light-emitting amount received via the radio means 7 into the storing means 40. The light-emitting amount varying means 10 can control the light-emitting amount in accordance with the information stored in the storing means 40. In this case, the radio means 7 of the capsule endoscope has a receiving and transmitting function.

As mentioned above, a number N in the case of emitting light with the light-emitting amount (e.g., L1, L2, . . . ) may be stored in the storing means 40 and the number of images in the case of the image pick-up operation with the different amount of illuminating light may be increased or reduced. Alternatively, the image may extracorporeally be monitored and the control operation may be performed, e.g., increasing the number N when the subject is near the examining target portion.

According to the fourth modification, the light can be emitted with the proper light-emitting amount in accordance with the examining target and the image can be obtained with small white compression or small black compression.

Although the illuminating means is the white LED 17, an organic EL (organic electroluminescence device) may be used as shown by parentheses in FIG. 11.

Second Embodiment

Figure 12A:
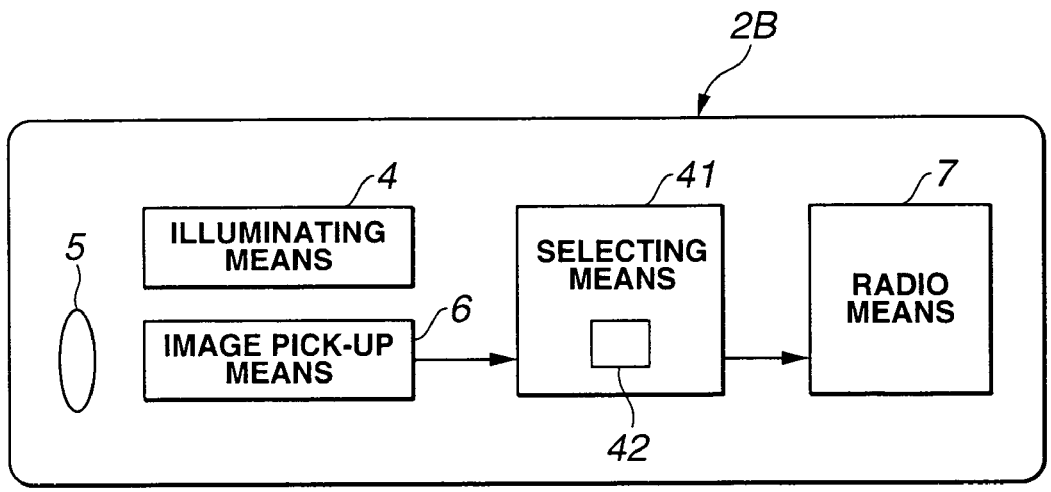

Next, the second embodiment of the present invention will be described with reference to FIGS. 12A and 12B. FIG. 12A schematically shows the structure of a capsule endoscope 2B according to the second embodiment of the present invention. According to the second embodiment, it is determined whether any of the two images picked up with the different amount of illuminating light has a wider dynamic range suitable to the diagnosis, the determined image is selected, and the selected image is transmitted to the extracorporeal device 3.

The capsule endoscope 2B further comprises selecting means 41 in the capsule endoscope 2 shown in FIG. 3. When the selecting means 41 converts the image obtained by the image pick-up means 6 into a digital signal and temporarily stores the converted signal in a memory, the selecting means 41 includes luminance distribution detecting means (luminance distribution estimating means) 42 which detects or estimates the schematic distribution of the luminance level.

The luminance distribution detecting means 42 detects the luminance distribution by the luminance distribution detecting means 42 in the image data picked up with the different light-emitting amount, selects the image data with the preferable luminance distribution, and transmits the selected image data to the extracorporeal device 3 from the radio means 7.

According to the second embodiment, referring to FIG. 5B, specifically, the capsule endoscope 2B includes a memory which stores two frames of the image data picked up in a state in which light is emitted with the light-emitting amount L1 and L2 for the time ta and tb (=ta). When the image data are stored in the memory, the luminance distribution estimating means 42 selects one image data with the preferable luminance distribution by using the selecting means 41. The selected image data is transmitted by the radio means 7. The other image data is not transmitted and the next image data is overwritten.

Figure 12B:
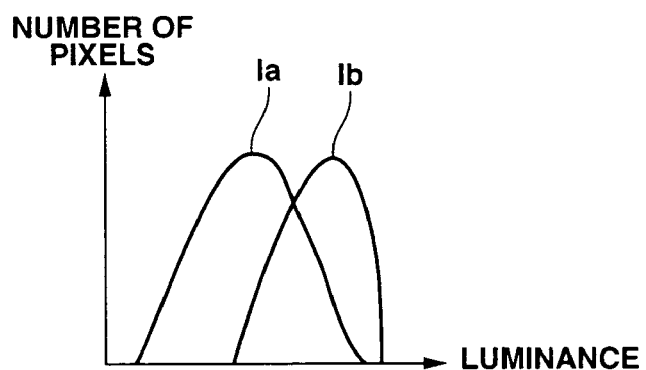
FIG. 12B is a diagram showing an example of the luminance distribution of two pieces of image data.

FIG. 12B shows an example of the luminance distributions of two images Ia and Ib picked up with the different light-emitting amount. The luminance distribution estimating means 42 calculates the schematic luminance distributions of the two images Ia and Ib, and transmits only the image data with the preferable luminance distribution based on the two luminance distributions.

In the case of determining the luminance distribution, the image with the distribution approximate to the Gaussian distribution may be determined as the image having the preferable luminance distribution or having the wide dynamic range with small white compression or small black compression. More briefly, the image having the wide luminance-range from the minimum value to the maximum value of the luminance level may be determined as the preferable image with the preferable luminance distribution or wide dynamic range.

In the example shown in FIG. 12B, the white compression is caused in the image Ib, and the image Ia without the white compression has the preferable luminance distribution. In this case, the image Ia has wider dynamic range. Therefore, only the image Ia is transmitted.

According to the second embodiment, the image data transmitted and recorded to the extracorporeal device 3 is only the more preferable image data. Therefore, there is a merit that the preferable image data remains later and the load of the editing operation such as the removal of unnecessary image data is omitted. Other structures have the same advantages as those according to the first embodiment. Although the case of the two pieces of the image data is described, in the case of three or more pieces of image data, only the image data determined as one having the most preferable luminance distribution or one having the widest dynamic range is transmitted.

Figure 12C:
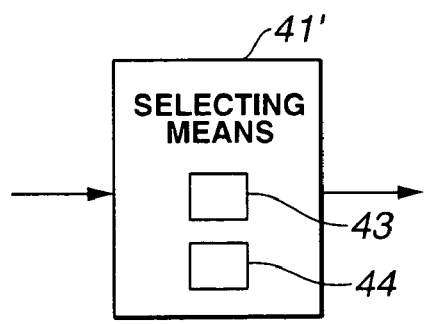
FIG. 12C is a diagram showing selecting means having data comparing means according to a first modification of the second embodiment.

In the foregoing, the image is selected based on the luminance distribution. However, the amount of image data may be compared upon converting the image data into the digital signal, compressing the digital signal, and temporarily storing the signal in the memory after compression, and the larger amount of image data may be transmitted to the extracorporeal device 3. FIG. 12C shows selecting means 41' in this case according to the first modification of the second embodiment. The selecting means 41' comprises compressing means 43 for compressing the image data and data amount comparing means 44 for comparing the amount of compressed data.

That is, generally, in the case of the image data having a large edge or contour, the amount of data after the compression is increased as compared with the case of the image data having the smaller edge or contour. Therefore, the image data having the large amount of data is transmitted to the extracorporeal device 3 as the image with the preferable quality.

Figure 13:
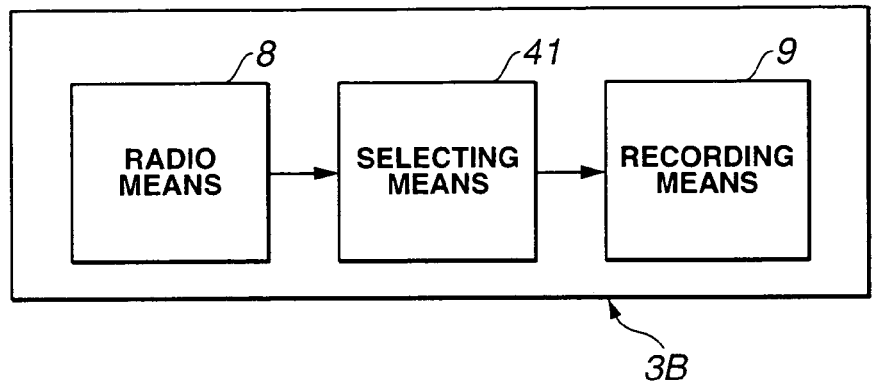

FIG. 13 shows an extracorporeal device 3B according to the second modification of the second embodiment. Referring to FIG. 12A, the capsule endoscope 2B side has the selecting means 41. According to the second modification, referring to FIG. 13, the selecting means 41 may be arranged to the extracorporeal device 3B side. In this case, the capsule endoscope shown in FIG. 1 can be used.

According to the second modification, similarly to the first embodiment, the capsule endoscope 2 transmits the entire picked-up image data to the extracorporeal device 3B. Then, in the extracorporeal device 3B, the luminance distribution detecting means 42 or the like detects the luminance distribution of the more preferable image. Further, the luminance distribution detecting means 42 determines the image with the preferable distribution, and records the determined image to the recording means 9.

In this case, after temporarily recording the received image data with the different amount of illuminating light, first, the image data with the unpreferable luminance distribution may be deleted from the recording means 9. Thus, a buffer memory can be reduced and the necessary capacity can be reduced.

Advantageously, the circuit structure of the capsule endoscope 2 side can be simplified by arranging the selecting means on the extracorporeal device 3B side. Advantageously, other structures are the same as those shown in FIG. 12A.

The selecting means 41 on the extracorporeal device 3B side may have means corresponding to the data amount comparing means 44 shown in FIG. 12C, thereby comparing the amount of the transmitted image data. Further, the larger amount of data may be recorded to the recording means 9. In this case, the same advantages as those in the case shown in FIG. 13 are obtained.

Third Embodiment

Figure 14:
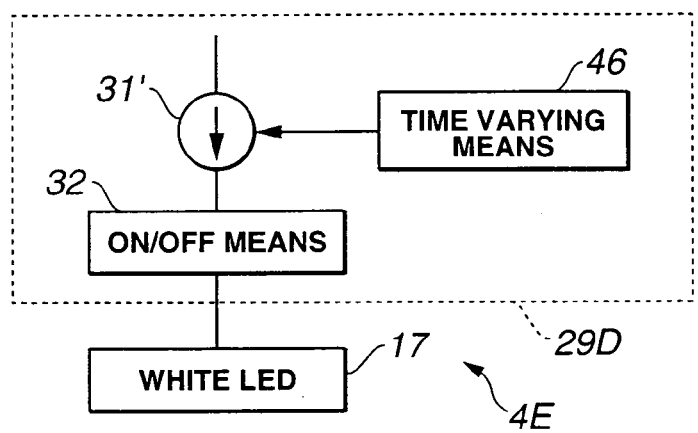
FIGS. 14 and 15 relate to a third embodiment of the present invention.

Next, the third embodiment of the present invention will be described with reference to FIG. 14. FIG. 14 shows the structure of illuminating means 4E according to the third embodiment. The illuminating means 4E has a light-emitting driving circuit 29C by using time varying means 46 in place of the light-emitting amount varying means 10 shown in FIG. 5A. In this case, a predetermined constant-current source 31' can be used in place of the variable constant-current source 31.

Figure 15:
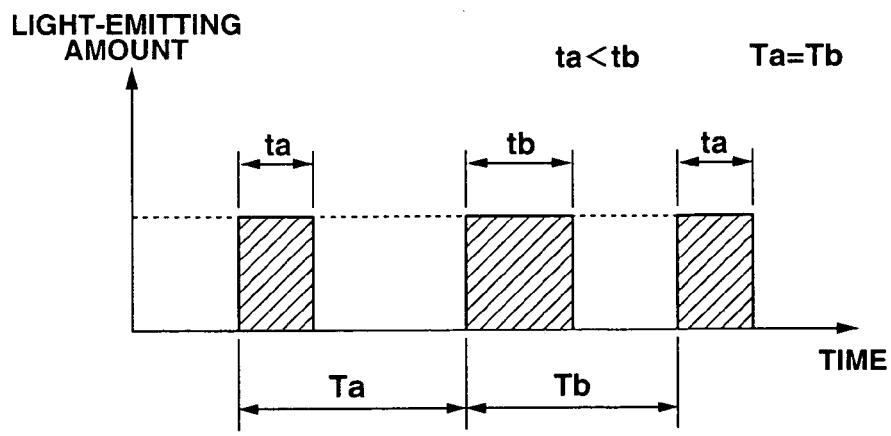

Referring to FIG. 15, the time varying means 46 is controlled by varying the time for switching on/off the ON/OFF means 32, namely, the light-emitting time.

In the case shown in FIG. 15, the white LED 17 emits light with the constant light-emitting amount (e.g., L1) by the constant-current source 31'. For example, at the light-emitting time ta and tb (ta<tb), the white LED 17 alternately emits light. Further, in this case, the image pick-up time Ta and Tb are the same and, however, they may be set to be different.

Other structures are the same as those according to the first embodiment. According to the third embodiment, the light-emitting time is changed and, thus, the same advantages as those in the case of changing the light-emitting amount according to the first embodiment are obtained.

In addition, on the image pick-up means 6 side, a plurality of image pick-up time may be set and then the image pick-up operation may be performed. For example, an element shutter using the image pick-up element 6a may function and the image pick-up operation may substantially be performed at different image pick-up time. In this case, advantageously, the same operations as those in the case of changing the light-emitting time are substantially obtained.

Fourth Embodiment

Figure 16:
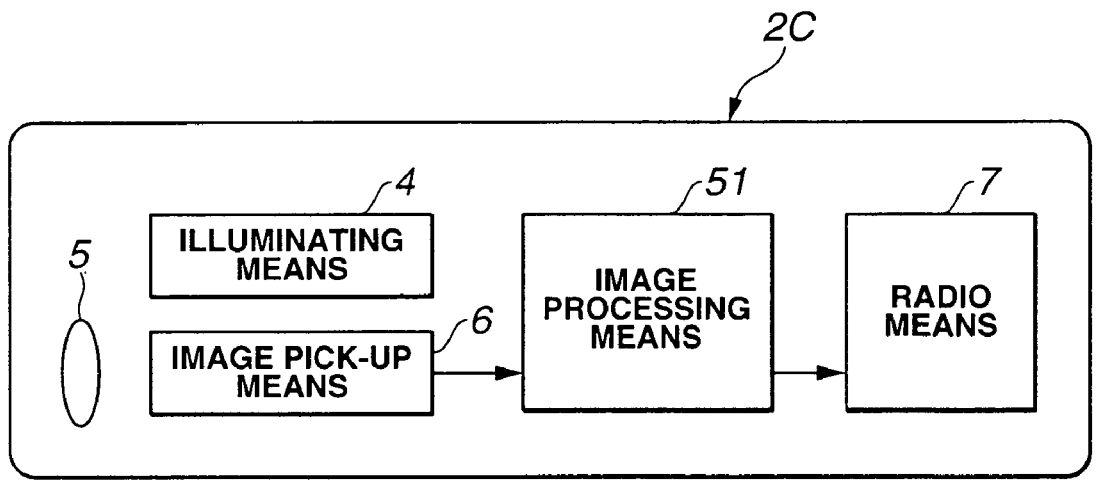
FIGS. 16 to 18 relate to a fourth embodiment of the present invention.

Next, the fourth embodiment of the present invention will be described with reference to FIG. 16. FIG. 16 schematically shows a capsule endoscope 2C according to the fourth embodiment. The capsule endoscope 2C is formed by arranging image processing means 51 in the capsule endoscope 2 according to the first embodiment.

The image processing means 51 combines two image signals picked up with the different amount of illuminating light outputted from the image pick-up means 6, generates one combined image with wide dynamic range (hereinafter, abbreviated to a D range), and transmits the generated image to the extracorporeal device 3 by using the radio means 7.

Figure 17:
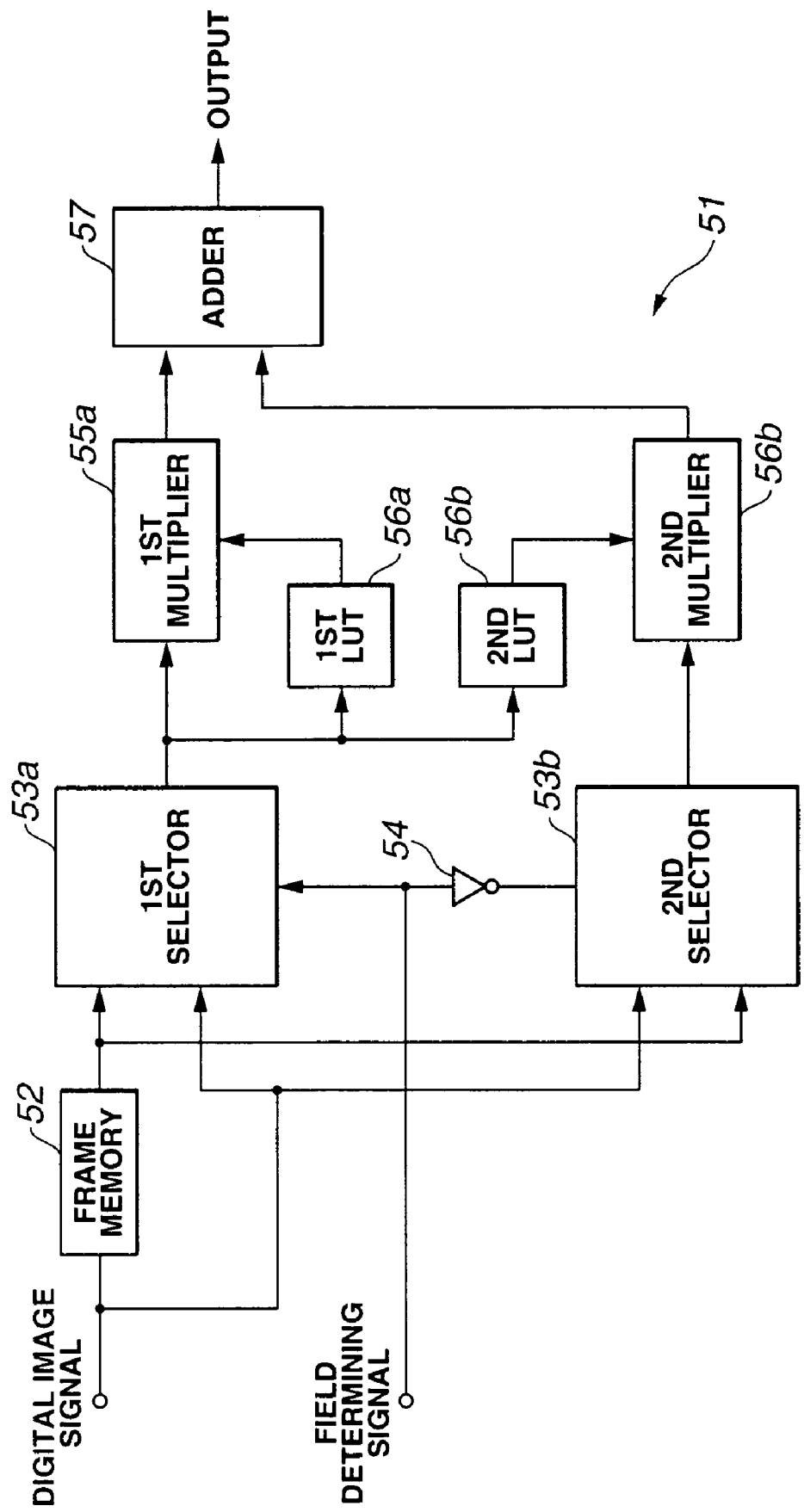

FIG. 17 shows the specific structure of the image processing means 51. In the following description, referring to FIG. 5B, the image picked up with the light-emitting amount L1 for the light-emitting time ta is referred to a first image and the image picked up with the light-emitting amount L2 for the light-emitting time tb is referred to a second image.

Referring to FIG. 17, digitally-converted first and second image signals which are sequentially inputted to a D range enlarging unit 51 are sequentially inputted to a frame memory 52. The image signals inputted to the frame memory 52 are delayed and inputted like FIFO (first-in first-out) to first and second selectors 53a and 53b every field term. That is, the signals are delayed for one field term and are outputted, thus to be outputted synchronously with the next-field signal.

A field determining signal is directly applied to the first selector 53a from the light-emitting varying means 10, and it is applied to the second selector 53b therefrom via an inverting circuit 54. The signal in the first or second field, which is inputted to the first selector 53a or the second selector 53b is captured based on the field determining signal.

The signal captured in the first selector 53a is outputted to a first multiplier 55a, is inputted to first and second look-up tables (LUTs) 56a and 56b, and is weighted with a proper function.

Here, as the function, the first LUT 56a is cos(pB)·cos(pB) and the second LUT 56b is sin(pB)·sin(pB). A variable pB in the function cos or sin converts a brightness B (luminance level of a pixel picked up with the small amount of illuminating light) of the subject, from 0 to $\pi/4$ or less by using a parameter p after scale conversion. The image data picked up under the condition of small amount of illuminating light is used because the image data includes a signal which is easily saturated depending on the case and such a case is prevented.

The function cos(pB) is a function which monotonously decreases for the brightness of the subject and the function sin(pB) is a function which monotonously increases. The squares of cos(pB) and sin(pB) exhibit the same property and, in this case, the addition of the squares of cos(pB) and sin(pB) is 1.

The signals weighted by the first and second LUT 56a and 56b are outputted to the first and second multipliers 55a and 55b, are multiplied to the signals outputted from the first and second selectors 53a and 53b. After that, the outputs of the first and second multipliers 55a and 55b are added by an adder 57, thus, a resultant signal becomes the image signal which is subjected to the D range enlargement processing, and it is outputted from the image processing means 51.

That is, the image processing means 51 increases the weight of the second image picked up with the large amount of illuminating light on the low-luminance side, and increases the weight of the first image picked-up with the small amount of illuminating light on the high-luminance side. Thus, the image is combined. It is possible to generate the image with the preferable image quality having the dynamic range wider than that using only one image.

The thus-generated image signal with the wide dynamic range is transmitted to the extracorporeal device 3 from the radio means 7, and is recorded to the recording means 9.

According to the fourth embodiment, the two images are picked up with the different amount of illuminating light and the image is generated from the two images with the enlarged D range. Thus, as compared with selecting one image, the image with high quality and without less white compression and black compression is obtained.

Figure 18:
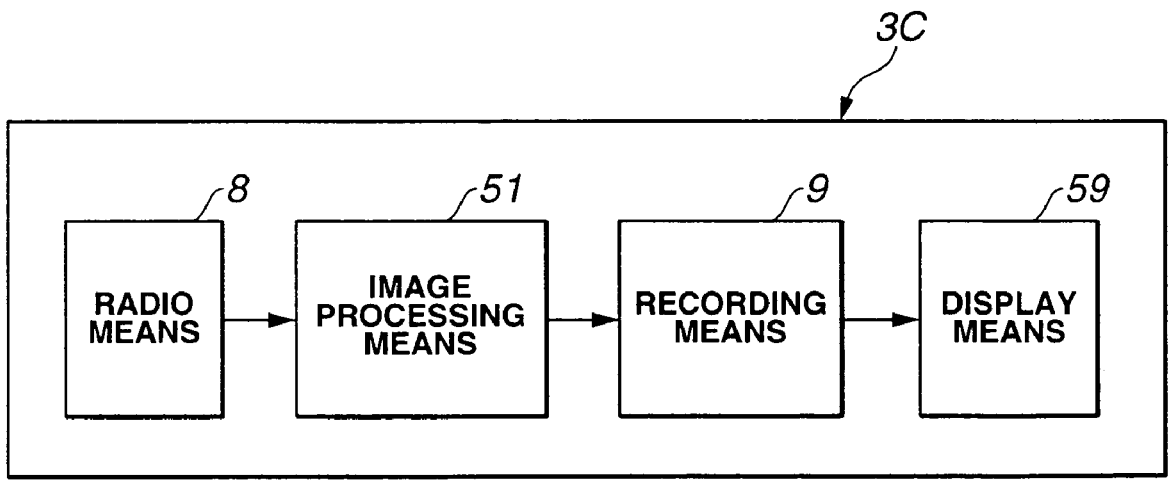

FIG. 18 schematically shows the structure of an extracorporeal device 3C according to a modification of the fourth embodiment. In the above description, the image processing means 51 is arranged to the capsule endoscope 2C. However, the image processing means 51 is arranged to the extracorporeal device 3C according to the modification.

Figure 1:
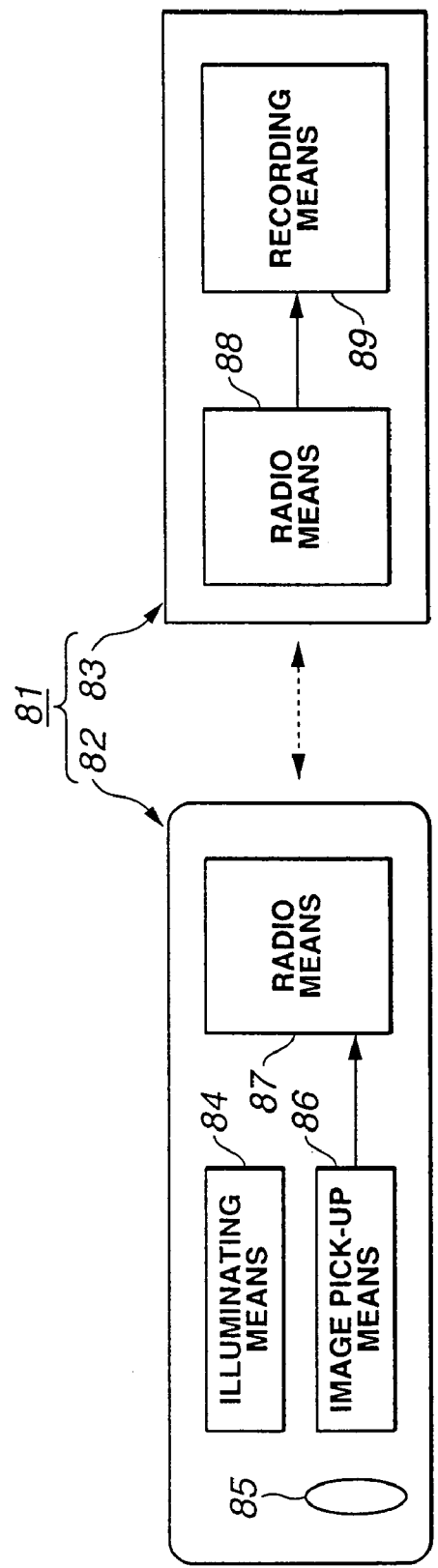
FIG. 1 is a diagram showing the entire structure of a capsule endoscope apparatus according to one conventional art.
Figure 2B:
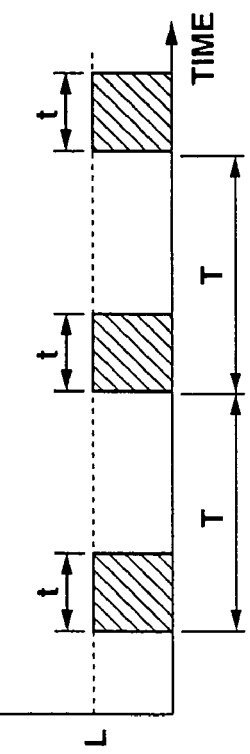
FIG. 2B is an explanatory diagram of the light-emitting operation according to the one conventional art.
Figure 2A:
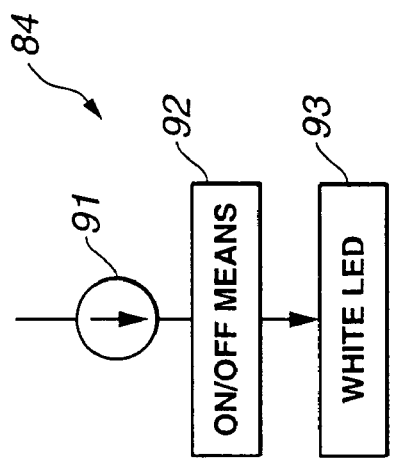
FIG. 2A is a diagram showing the structure of illuminating means according to the one conventional art.

According to the modification, the extracorporeal device 3 shown in FIG. 1 has the image processing means 51. Further, the combined image recorded to the recording means 9 is displayed on display means 59.

Further, according to the modification, one image is combined with the wide D range based on the first image and second image in the image data transmitted from the capsule endoscope 2, and is recorded to the recording means 9, and the combined image recorded to the recording means 9 is displayed on the display means 59.

Furthermore, it is possible to obtain the image with high quality which results in easy diagnosis on the extracorporeal device 3 side without increasing the circuit scale of the capsule endoscope 2.

Fifth Embodiment

Figure 19:
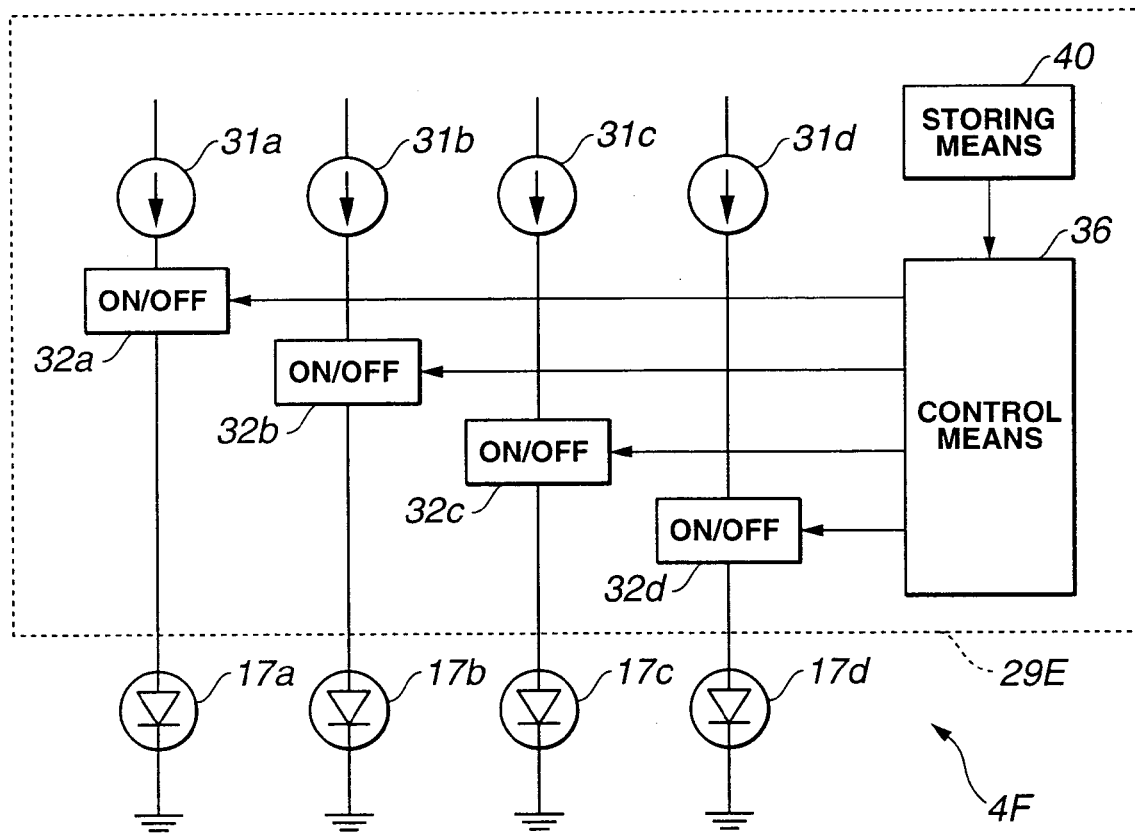
FIGS. 19 and 20 relate to a fifth embodiment.

Next, the fifth embodiment of the present invention will be described with reference to FIG. 19. FIG. 19 shows the structure of illuminating means 4F according to the fifth embodiment. The illuminating means 4C shown in FIG. 8 controls the light emission based on the unit of the two white LEDs. However, according to the fifth embodiment, the white LED is arbitrarily selected based on the unit of one white LED 17$i$ (I=a to d) so as to control the light emission. Further, a light-emitting driving circuit 29E having the storing means 40 shown in FIG. 11 controls the selection of the white LED 17$i$ which emits light by information stored in the storing means 40.

That is, referring to FIG. 19, a constant-current source 31$i$ is connected to the white LED 17$i$ via ON/OFF means 32$i$, and the ON/OFF means 32$i$ is controlled for the on/off operation by the control means 36.

According to the fifth embodiment, based on the information in the storing means 40, the white LED 17$i$ emits light as shown in FIG. 9 and further the property of light distribution for the illuminating light can be changed by varying the combination of the white LED 17$i$ which emits light.

Moreover, according to the fifth embodiment, when the property of light distribution changes, a plurality of images are obtained with the same light-emitting amount (amount of illuminating light). For example, referring to FIG. 9, in the cycle, two images are obtained with the different amount of illuminating light. However, for example, referring to FIG. 20, in the cycle, two images are obtained with the different amount of illuminating light and further three images are obtained in consideration of the change in property of light distribution.

Through the illumination which enables the change in property of light distribution, in particular, through the illumination at the approximated near-point, the white LED at the most approximated near-point does not emit light but the white LED on the opposite side emits light, thus to obtain the image with high quality without the white compression.

Figure 20:
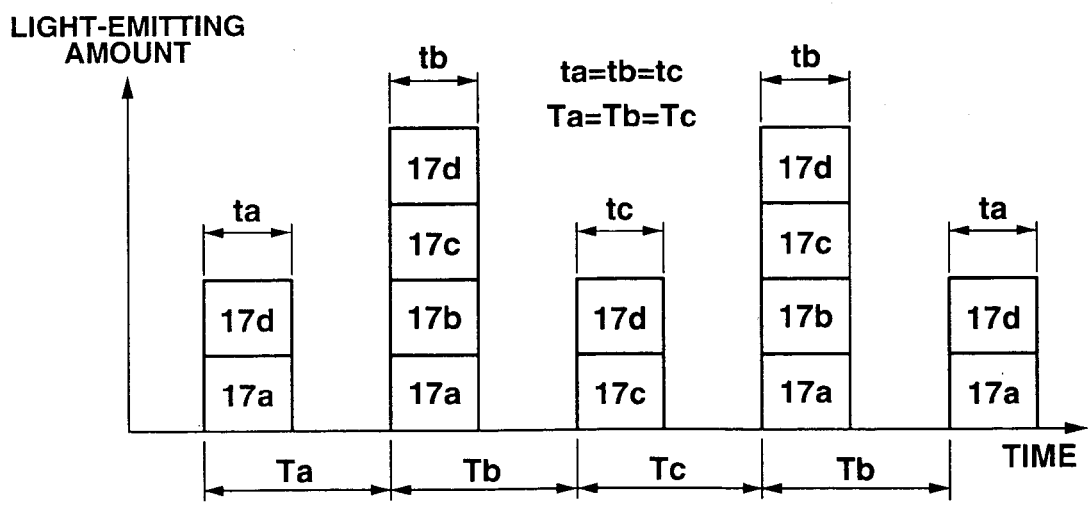

Therefore, referring to FIG. 20 or the like, a plurality of images are picked up by changing the property of light distribution as a result of changing the white LED which emits light with the same amount of illuminating light. The plurality of picked-up images may be transmitted to the extracorporeal device 3 as mentioned above according to the first embodiment, or the image may be selected with the high quality and be transmitted to the extracorporeal device according to the second embodiment.

According to the fifth embodiment, since the property of light distribution changes, thereby obtaining the plurality of images, it is possible to obtain the image with high quality without white compression, particularly, at the near-point.

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. A capsule endoscope apparatus comprising:
an illuminating device for illuminating a body cavity;
a switching device which automatically changes at least one illuminating variable from one image acquisition cycle to a next image acquisition cycle in order to provide a difference in illuminating condition between the image acquisition cycles, wherein at least two different illuminating variables comprising a light-emitting amount and a light-emitting time, as well as the change in at least one illuminating variable between image acquisition cycles, are preset, the illuminating light having the same wavelength band from one image acquisition cycle to the next image acquisition cycle;
an image pick-up device for sequentially picking up image data of the body cavity under the different illumination conditions;
a setting device which sets the light-emitting amount or light-emitting time; and
a radio device for extracorporeally transmitting the image data obtained under each of the different illuminating conditions by the image pick-up device.

2. A capsule endoscope apparatus according to claim 1, wherein the setting device is a storing device which stores information for setting the light-emitting amount or light-emitting time.

3. A capsule endoscope apparatus according to claim 1, wherein the illuminating device comprises a white LED.

4. A capsule endoscope apparatus according to claim 1, wherein the illuminating device comprises an electroluminescence.

5. A capsule endoscope apparatus according to claim 1, wherein a signal gain of the image pick-up device is proportional to the light-emitting amount or light-emitting time.

6. A capsule endoscope apparatus according to claim 1, wherein the two different illuminating conditions and the switching order thereof preset by the switching device are set to be changeable by a radio signal.

7. A capsule endoscope apparatus comprising:
an illuminating device for illuminating a body cavity;
a switching device which automatically changes at least one illuminating variable from one image acquisition cycle to a next image acquisition cycle in order to provide a difference in illuminating condition between the image acquisition cycles, wherein at least two different illuminating variables comprising a light-emitting amount and a light-emitting time, as well as the change in at least one illuminating variable between image acquisition cycles, are preset, the illuminating light having the same wavelength band from one image acquisition cycle to the next image acquisition cycle;
an image pick-up device for sequentially picking up image data of the body cavity under the different illuminating condition;
a selecting device which extracts an image with a wide dynamic range from two or more pieces of image data obtained by the image pick-up device; and
a setting device which sets the light-emitting amount or light-emitting time; and a radio device which transmits by radio waves the image data obtained by the selecting device.

8. A capsule endoscope apparatus according to claim 7, wherein a luminance distribution of the image data is used as a comparison standard for extracting the image with a wide dynamic range by the selecting device.

9. A capsule endoscope apparatus according to claim 7, wherein an amount of data after compressing the image data is used as a comparison standard for extracting the image with a wide dynamic range by the selecting device.

10. A capsule endoscope apparatus according to claim 7, wherein the two different illuminating conditions and the switching order thereof preset by the switching device are set to be changeable by a radio signal.

11. A capsule endoscope apparatus having an illuminating device, an image pick-up device for picking up an image of an illuminated portion, and a radio transmitting device, the capsule endoscope apparatus comprising:
    the illuminating device comprising a switching device which switches one of a light-emitting amount and a light-emitting time;
    a selecting device which extracts an image with a wide dynamic range from the two or more pieces of image data obtained by the image pick-up device upon sequentially switching one of the light-emitting amount and light-emitting time; and
    a radio device which transmits by radio waves the image data obtained by the selecting device;
    wherein a luminance distribution of the image data is used as a comparison standard for extracting the image with a wide dynamic range by the selecting device and the selecting device selects the image data with a widest luminance distribution of the image data.

12. A capsule endoscope apparatus having an illuminating device, an image pick-up device for picking up an image of an illuminated portion, and a radio transmitting device, the capsule endoscope apparatus comprising:
    the illuminating device comprising a switching device which switches one of a light-emitting amount and a light-emitting time;
    a selecting device which extracts an image with a wide dynamic range from the two or more pieces of image data obtained by the image pick-up device upon sequentially switching one of the light-emitting amount and light-emitting time; and
    a radio device which transmits by radio waves the image data obtained by the selecting device;
    wherein an amount of data after compressing the image data is used as a comparison standard for extracting the image with a wide dynamic range by the selecting device and the selecting device selects the image having a largest amount of compressed image data.

13. A capsule endoscope apparatus comprising:
    an illuminating device for illuminating a body cavity;
    a switching device which automatically changes at least one illuminating variable from one image acquisition cycle to a next image acquisition cycle in order to provide a difference in illuminating condition between the image acquisition cycles, wherein at least two different illuminating variables comprising a light-emitting amount and a light-emitting time, as well as the change in at least one illuminating variable between image acquisition cycles, are preset, the illuminating light having the same wavelength band from one image acquisition cycle to the next image acquisition cycle;
    an image pick-up device for sequentially picking up image data of the body cavity under the different illuminating conditions;
    a setting device which sets the light-emitting amount or light-emitting time;
    a radio device which transmits by radio waves the image data obtained by the image pick-up device;
    a selecting device which extracts an image with a wide dynamic range from two or more pieces of transmission image data transmitted by the radio device; and
    a recording device which records the transmitted image data selected by the selecting device.

14. A capsule endoscope apparatus according to claim 13, wherein a luminance distribution of the transmitted image data is used as a comparison standard for extracting the image with the wide dynamic range by the selecting device.

15. A capsule endoscope apparatus according to claim 13 wherein an amount of data after compressing the transmitted image data is used as a comparison standard for extracting the image with the wide dynamic range by the selecting device.

16. A capsule endoscope apparatus according to claim 13, wherein the two different illuminating conditions and the switching order thereof preset by the switching device are set to be changeable by a radio signal.

17. A capsule endoscope system having an illuminating device, an image pick-up device for picking up an image of an illuminated portion, and a radio transmitting device, the capsule endoscope system comprising:
    the illuminating device comprising a switching device which switches one of a light-emitting amount and light-emitting time;
    a selecting device which transmits two or more pieces of image data obtained by the image pick-up device by the radio transmitting device upon sequentially switching one of the light-emitting amount and light-emitting time, and extracts the image with a wide dynamic range from the two or more images transmitted by the radio transmitting device; and
    a recording device which records the transmitted image data selected by the selecting device;
    wherein a luminance distribution of the transmitted image data is used as a comparison standard for extracting the image with the wide dynamic range by the selecting device and the selecting device selects the transmitted image data with a largest luminance distribution of the transmitted image data.

18. A capsule endoscope system having an illuminating device, an image pick-up device for picking up an image of an illuminated portion, and a radio transmitting device, the capsule endoscope system comprising:
    the illuminating device comprising a switching device which switches one of a light-emitting amount and light-emitting time;
    a selecting device which transmits two or more pieces of image data obtained by the image pick-up device by the radio transmitting device upon sequentially switching one of the light-emitting amount and light-emitting time, and extracts the image with a wide dynamic range from the two or more images transmitted by the radio transmitting device; and
    a recording device which records the transmitted image data selected by the selecting device;
    wherein an amount of data after compressing the transmitted image data is used as a comparison standard for extracting the image with the wide dynamic range by the selecting device and the selecting device selects the image having a largest amount of the compressed and transmitted image data.

19. A capsule endoscope apparatus comprising:

an illuminating device for illuminating a body cavity;

a switching device which automatically changes at least one illuminating variable from one image acquisition cycle to a next image acquisition cycle in order to provide a difference in illuminating condition between the image acquisition cycles, wherein at least two different illuminating variables comprising a light-emitting amount and a light-emitting time, as well as the change in at least one illuminating variable between image acquisition cycles, are preset, the illuminating light having the same wavelength band from one image acquisition cycle to the next image acquisition cycle;

an image pick-up device for sequentially picking up image data of the body cavity under the different illuminating conditions;

a setting device which sets the light-emitting amount or light-emitting time;

a radio device which transmits by radio waves image data obtained by the image pick-up device;

an image processing device which generates one piece of combined image with an enlarged dynamic range from two or more pieces of transmission image data transmitted by the radio device;

a memory device which stores the combined image; and a display device which displays the combined image.

20. A capsule endoscope apparatus according to claim 19, wherein the two different illuminating conditions and the switching order thereof preset by the switching device are set to be changeable by a radio signal.

21. A capsule endoscope apparatus comprising:

an illuminating device for illuminating a body cavity;

a switching device which automatically changes at least one illuminating variable from one image acquisition cycle to a next image acquisition cycle in order to provide a difference in illuminating condition between the image acquisition cycles, wherein at least two different illuminating variables comprising a light-emitting amount and a light-emitting time, as well as the change in at least one illuminating variable between image acquisition cycles, are preset, the illuminating light having the same wavelength band from one image acquisition cycle to the next image acquisition cycle;

an image pick-up device for sequentially picking up image data of the body cavity under the different illuminating conditions;

a setting device which sets the light-emitting amount or light-emitting time;

an image processing device which generates one piece of combined image with an enlarged dynamic range from two or more pieces of image data obtained by the image pick-up device; and a radio device which transmits by radio waves the combined image.

22. A capsule endoscope apparatus according to claim 21, wherein the two different illuminating conditions and the switching order thereof preset by the switching device are set to be changeable by a radio signal.

23. A capsule endoscope apparatus comprising:

an illuminating device for illuminating a body cavity;

a switching device which automatically changes at least one illuminating variable from one image acquisition cycle to a next image acquisition cycle in order to provide a difference in illuminating condition between the image acquisition cycles, wherein at least two different illuminating variables comprising a light-emitting amount and a light-emitting time, as well as the change in at least one illuminating variable between image acquisition cycles, are preset, the illuminating light having the same wavelength band from one image acquisition cycle to the next image acquisition cycle;

an image pick-up device for sequentially picking up image data of the body cavity under the different illuminating conditions;

a setting device which sets the light-emitting amount or light-emitting time; and a radio device which transmits by radio waves the image data obtained by the image pick-up device.

24. A capsule endoscope apparatus according to claim 23, wherein the light emitting element comprises a plurality of light-emitting elements at different arranging positions, and the switching device selects the light-emitting element which emits light from the plurality of light emitting elements and changes the property of light distribution for the illuminating light.

25. A capsule endoscope apparatus according to claim 23, wherein the two different illuminating conditions and the switching order thereof preset by the switching device are set to be changeable by a radio signal.

* * * * *